US00PP32841P2

(12) United States Plant Patent
Boxriker

(10) Patent No.: US PP32,841 P2
(45) Date of Patent: Feb. 23, 2021

(54) ***OSTEOSPERMUM* PLANT NAMED 'KLEOE19395'**

(50) Latin Name: ***Osteospermum ecklonis* Norl**
Varietal Denomination: KLEOE19395

(71) Applicant: Klemm+Sohn GmbH & Co. KG, Stuttgart (DE)

(72) Inventor: Maike Boxriker, Schwäbisch Gmünd (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 16/867,672

(22) Filed: May 6, 2020

(51) Int. Cl.
*A01H 5/02* (2018.01)
*A01H 6/14* (2018.01)

(52) U.S. Cl.
USPC ..... Plt./360
CPC ..... *A01H 6/148* (2018.05)

(58) Field of Classification Search
USPC ..... Plt./360
CPC ..... A01H 6/148; A01H 5/02
See application file for complete search history.

*Primary Examiner* — Keith O. Robinson
(74) *Attorney, Agent, or Firm* — Weatherly IP Solutions, LLC; James Weatherly

(57) ABSTRACT

A new *Osteospermum* plant particularly distinguished by having yellow flower color with a dark purple eye and a compact plant habit.

1 Drawing Sheet

Genus and species: *Osteospermum ecklonis* Norl.
Variety denomination: 'KLEOE19395'.

BACKGROUND OF THE NEW PLANT

The present invention comprises a new and distinct variety of *Osteospermum*, botanically known as *Osteospermum ecklonis* Norl, and hereinafter referred to by the variety name 'KLEOE19395'. 'KLEOE19395' originated from a cross-pollination between the proprietary female *Osteospermum* variety 'OE-2013-0045' (unpatented), and the commercial male *Osteospermum* variety 'Balostlueye' (U.S. Plant Pat. No. 26,150).

In the summer of 2015, the two *Osteospermum* parental lines 'OE-2013-0045' and 'Balostlueye' were crossed in Nairobi, Kenya, and seeds were obtained. The seeds were sown and plants were grown for evaluation. The seedling was selected in spring of 2016 and named 'KLEOE19395'. In fall of 2015, 'KLEOE19395' was first vegetatively propagated by vegetative cuttings in Stuttgart, Germany. 'KLEOE19395' was found to reproduce true to type in successive generations of asexual propagation via vegetative cuttings.

SUMMARY

The following are the most outstanding and distinguishing characteristics of this new variety when grown under normal horticultural practices in Stuttgart, Germany.

1. Yellow flower color with a dark purple eye; and
2. Compact habit.

DESCRIPTION OF THE PHOTOGRAPH

This new *Osteospermum* plant is illustrated by the accompanying photograph, which shows the plant with flowers grown in a pot. The photograph is of an eleven-week-old plant grown in a controlled greenhouse environment in Stuttgart, Germany in May 2019. The colors shown are as true as can be reasonably obtained by conventional photographic procedures.

DESCRIPTION OF THE NEW VARIETY

The following detailed descriptions set forth the distinctive characteristics of 'KLEOE19395'. The data which define these characteristics were collected from asexual reproductions carried out in Latina, Italy. Data was collected on nineteen-week-old plants grown in a controlled greenhouse environment in Latina, Italy under greenhouse conditions in February 2020. Color references are to The R.H.S. Colour Chart of The Royal Horticultural Society of London (R.H.S.), 5$^{th}$ edition (2007).

Classification:
- *Family*.—Compositae.
- *Botanical*.—*Osteospermum ecklonis* Norl.
- *Common*.—*Osteospermum*, African Daisy.
- *Designation*.—'KLEOE19395'.

Parentage:
- *Female parent*.—*Osteospermum* line 'OE-2013-0045' (unpatented).
- *Male parent*.—*Osteospermum* line 'Balostlueye' (U.S. Plant Pat. No. 26,150).

Plant:
- *Form and habit*.—Herbaceous perennial, but usually cultivated as an annual; not frost resistant.
- *Growth habit*.—Upright.
- *Branching habit*.—Normal.
- *Height (from top of soil, including inflorescence)*.—38.0 cm.
- *Width (including inflorescences)*.—30.0 cm.
- *Propagation*.—Vegetative cuttings.
- *Time to produce a finished flowering plant*.—9 weeks.
- *Time to initiate and develop roots*.—5 weeks.
- *Root description*.—Fine; white.

Leaves:
*Arrangement*.—Alternate.
*Shape*.—Obovate.
*Apex*.—Acute.
*Base*.—Acute.
*Margin*.—Serrate.
*Immature color*.—Upper surface: RHS 137C. Lower surface: RHS 137D.
*Mature color*.—Upper surface: RHS 146A. Lower surface: RHS 146C.
*Length*.—7.1 cm.
*Width*.—2.5 cm.
*Texture*.—Upper surface: Leathery. Lower surface: Leathery smooth, covered with fine hairs.
*Petioles*.—Absent.
*Venation pattern*.—Pinnate.
*Venation color*.—Upper surface: RHS 144A. Lower surface: RHS N144A.

Stems:
*Total number of branches per plant* (*calculated at the base of the plant*).—4.
*Length*.—30.0 cm.
*Diameter*.—0.6 cm.
*Internode length*.—2.3 cm.
*Color*.—RHS 144B.
*Texture*.—Smooth.
*Anthocyanin*.—RHS N77A.

Buds:
*Shape*.—Round to ovoid.
*Length*.—0.7 cm.
*Diameter*.—1.2 cm.
*Color* (*at tight bud just before the ray florets unfold*).—RHS 144B.

Inflorescence:
*Type*.—Composite, single.
*Blooming habit*.—Upright, with long flower stems.
*Quantity of inflorescences per plant*.—2.
*Lastingness of the inflorescences on the plant*.—10 to 15 days.
*Fragrance*.—Slightly present; fresh.
*Inflorescence diameter*.—7.0 cm.
*Inflorescence depth*.—1.0 cm.
*Disc diameter*.—1.8 cm.

Disc floret:
*Quantity per inflorescence*.—About 100.
*Shape*.—Tubular.
*Tube color*.—Closed: RHS N155B. Mature: RHS 155A.
*Length*.—0.5 cm.
*Diameter* (*at apex*).—0.2 cm.
*Apex*.—Acute.
*Apex color*.—RHS N155A.
*Base*.—Acute.
*Base color*.—RHS 155A.
*Margin*.—Entire.

Ray floret:
*Quantity per inflorescence*.—23.
*Shape*.—Oblanceolate.
*Color*.—Upper surface: RHS 12A with an RHS N79B Ring. Lower surface: RHS N81B.
*Length*.—3.2 cm.
*Width*.—0.9 cm.
*Apex*.—Acute.
*Base*.—Acute.
*Margin*.—Entire.
*Texture*.—Upper and lower surfaces: Smooth.
*Peduncle*.—Length: 13.0 cm. Diameter: 0.3 cm. Texture: Smooth with hairs. Color: RHS 144A with RHS N77A anthocyanin coloration.

Phyllaries:
*Texture*.—Smooth with fine hairs.
*Color*.—RHS 144A.
*Arrangement*.—Single.
*Observed quantity per plant*.—22.
*Shape*.—Lanceolate.
*Color*.—Upper surface: RHS 144A. Lower surface: RHS 144D.
*Length*.—1.2 cm.
*Width*.—0.2 cm.
*Apex*.—Acute.
*Base*.—Obtuse.
*Margin*.—Entire.
*Texture*.—Upper surface: Smooth with fine hairs. Lower surface: Smooth.

Reproductive organs:
*Androecium*.—Location: On the disc floret. Stamens: Quantity: Numerous. Shape: Filamentous. Filament length: 0.4 cm. Filament diameter: Less than 0.1 cm. Anther: Shape: Lanceolate. Color: RHS N79A. Length: Less than 0.1 cm. Diameter: Less than 0.1 cm. Pollen: Color: RHS 21A. Amount: Moderate.
*Gynoecium*.—Location: On the base of the petals (ray floret) and reduced on disc florets. Pistils: Number: Numerous. Length: 0.3 cm. Diameter: Less than 0.1 cm. Stigma: Color: RHS N79A. Shape: Filamentous. Length: 0.2 cm. Diameter: Less than 0.1 cm. Style: Color: RHS N79A. Length: 0.1 cm. Diameter: Less than 0.1 cm.

Fruit and seed set: None observed.

Disease and pest/insect resistance: No particular disease or insect resistance observed.

COMPARISON WITH PARENTAL LINES AND KNOWN VARIETY

'KLEOE19395' is distinguished from its parents as described in Table 1:

TABLE 1

Comparison with Parental Lines

| Trait | Variety 'KLEOE19395' | Female parent 'OE-2013-0045' | Male Parent 'Balostlueye' |
|---|---|---|---|
| Flower color | Yellow with dark purple eye | Yellow with light purple eye | Yellow with purple eye |

'KLEOE19395' is most similar to the *Osteospermum* plant named 'KLEOE12197' (unpatented). Differences between the two varieties are described in Table 2:

TABLE 2

Comparison with Similar Variety

| Trait | Variety 'KLEOE19395' | Commercial line 'KLEOE12197' |
|---|---|---|
| Flower Color | Yellow with dark purple eye | Pink with white eye |
| Habit | Compact | Very compact |

I claim:

1. A new and distinct variety of *Osteospermum* plant named 'KLEOE19395' as shown and described herein.

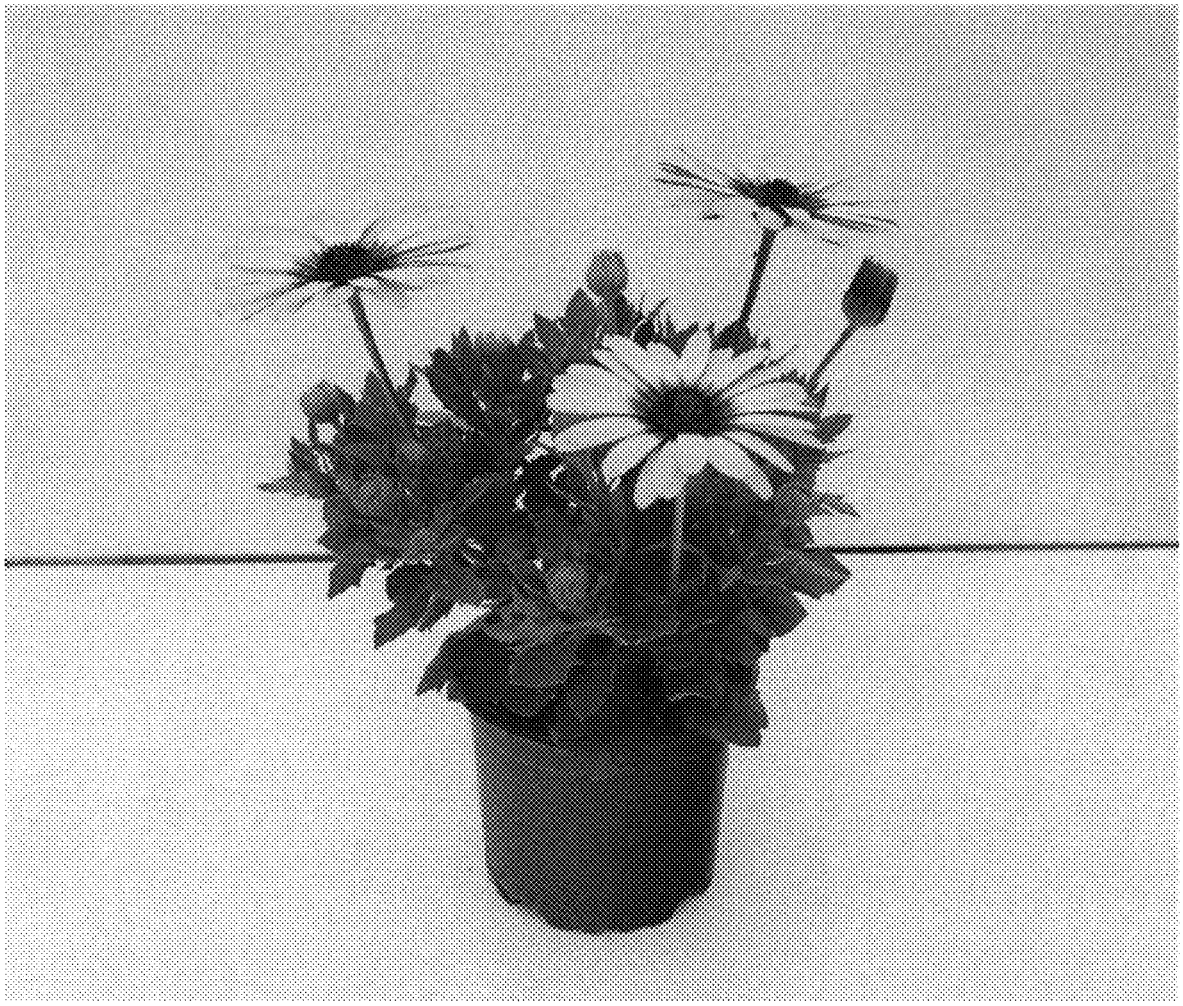

* * * * *